United States Patent [19]
Kuo et al.

[11] Patent Number: 5,783,671
[45] Date of Patent: *Jul. 21, 1998

[54] METHOD AND COMPOSITION FOR PREPARATION OF FACTOR VIIIC

[75] Inventors: George Kuo; Frank Masiarz, both of San Francisco; Martha Truett, Oakland; Pablo Valenzuela, San Francisco, all of Calif.; Mirella Ezban Rasmussen, Copenhagen, Denmark; Jennifer M. Favaloro, Victoria, Australia

[73] Assignees: Chiron Corporation, Emveryville, Calif.; Novo Nordisk A/S, Bagsvaerd, Denmark

[*] Notice: The portion of the term of this patent subsequent to Dec. 29, 2004, has been disclaimed.

[21] Appl. No.: 143,527

[22] Filed: Oct. 26, 1993

Related U.S. Application Data

[63] Continuation of Ser. No. 669,680, Mar. 14, 1991, abandoned, which is a continuation of Ser. No. 570,062, Jan. 12, 1984, Pat. No. 5,004,804.

[51] Int. Cl.$^6$ ........................................... C07K 16/36
[52] U.S. Cl. ........................ 530/388.25; 530/388.1; 530/389.3
[58] Field of Search ........................ 530/388.1, 388.25, 530/389.3

[56] References Cited

U.S. PATENT DOCUMENTS

| | | | |
|---|---|---|---|
| Re. 32,011 | 10/1985 | Zimmerman et al. | |
| 4,419,446 | 12/1983 | Howley et al. | 435/68 |
| 4,649,132 | 3/1987 | Zimmerman et al. | 514/12 |
| 4,657,894 | 4/1987 | Zimmerman et al. | 514/12 |
| 4,716,117 | 12/1987 | Kuo et al. | 435/240.27 |
| 5,004,804 | 4/1991 | Kuo et al. | 530/387 |
| 5,362,854 | 11/1994 | Zimmerman et al. | 530/383 |

FOREIGN PATENT DOCUMENTS

| | | |
|---|---|---|
| 083 483 | 7/1983 | European Pat. Off. |
| 0 123 945 | 11/1984 | European Pat. Off. |
| 1 157 556 | 10/1985 | European Pat. Off. |
| 0 160 457 | 11/1985 | European Pat. Off. |
| 0 182 372 | 5/1986 | European Pat. Off. |
| WO 84/04541 | 11/1984 | WIPO |
| WO 85/01961 | 5/1985 | WIPO |

OTHER PUBLICATIONS

Bloom, Haemophilia: Benefits of cloning genes for clotting factors, (1983) *Nature* 303:474–475.
Chan et al., Cell-free synthesis of factor VIII–related protein, (1984) *Chem. Abstracts* 100:214 (abstract No. 63605e).
Choo et al., Molecular cloning of the gene for human anti-haemophilic factor IX, (1982) *Nature* 299:178–180.
Fay et al., Purification and characterization of a highly purified human factor VIII consisting of a single type of polypeptide chain, (1982) *Proc. Natl. Acad. Sci. USA* 79:7200–7204.

Fulcher et al., Characterization of the human factor VIII procoagulant protein with a heterologous precipitating antibody, (1982) *Proc. Natl. Acad. Sci. USA* 79:1648–1652.
Fulcher et al., Proteoplytic inactivation of human factor VIII procoagulant protein by activated human protein C and its analogy with Factor V, (1984) *Blood* 63:486–489.
Fulcher et al., Human factor VIII procoagulant protein: Monoclonal antibodies define precursor–product relationships and functional epitopes, (1985) *J. Clin. Invest.* 76:117–124.
Ginsberg et al., Human von Willebrand factor (vWF): Isolation of complementary DNA (cDNA) clones and chromosomal localization, (1985) *Science* 228:1401–1406.
Gitschier et al., Characterization of the human factor VIII gene, (1984) *Nature* 312:326–330.
Kaufman et al., Construction of a modular dihydrofolate reductase cDNA gene: Analysis of signals utilized for efficient for efficient expression, (1982) *Mol. Cell. Biol.* 2:1304–1319.
Kuo et al., Studies on the molecular structure of human factor VIII:C, (1983) *Abst. for XI Int'l Cong. Thromb. Haemostasis* 50:262 (abstract # 0818).
Kurachi et al., Isolation and characterization of a cDNA coding for human factor IX, (1982) *Proc. Natl. Acad. Sci. USA* 79:6461–6464.
Maddox, Factor VIII cloning, (1983) *Nature* 306:528.
Maniatis et al., *Molecular Cloning: A Laboratory Manual* (1982) pp. 224–228.
Muller et al., A monoclonal antibody to VIII:C produced by a mouse hybridoma, (1981) *Blood* 58:1000–1006.
Muller et al., A monoclonal antibody to VIII:C produced by mouse hybridoma, (1982) *Chem. Abstracts* 96:480.
Nordfang et al., Specificity of monoclonal antibodies to factor VIII:C, (1985) *Thromb. Haemostas.* 54:586–590.
Rotblat et al., Monoclonal antibodies tohuman procoagulant factor VIII, (1984) *Biol. Abstracts* 77:4443.
Rotblat et al., Monoclonal antibodies to human procoagulant factor VIII, (1983) *J. Lab. Clin. Med.* 101:736–746.
Toole et al., Molecular cloning of a cDNA encoding human antihaemophilic factor, (1984) *Nature* 312:342–347.
Vehar et al., Structure of human factor VIII, (1984) *Nature* 312:337–342.

(List continued on next page.)

*Primary Examiner*—Donald E. Adams
*Attorney, Agent, or Firm*—Amy L. Collins; Grant D. Green; Robert P. Blackburn

[57] ABSTRACT

Methods and compositions are provided for recombinant DNA production of Factor VIIIC and truncated derivatives thereof. Based on amino acid sequences, probes are developed for isolating messenger RNA and/or chromosomal DNA encoding for Factor VIIIC. The Factor VIIIC gene in its entirety or encoding for a fragment thereof is then used for expression of Factor VIIIC in a host. The bacteriophage λFVIII23D containing the 14.43 kb EcoRI fragment was deposited at the A.T.C.C. on Jan. 4, 1984 and given Accession No. 40094.

1 Claim, No Drawings

OTHER PUBLICATIONS

Wood et al., Expression of active human factor VIII from recombinant DNA clones, (1984) *Nature* 312:330–337.

Austen, The chromatographic separation of factor VIII on aminohexyl sepharose, (1979) *Br. J. Haematol.* 43:669–674.

Fass et al., Monoclonal antibodies to porcine factor VIII coagulant and their use in the isolation of active coagulant, (1982) *Blood* 59:594–600.

Fulcher et al., Thrombin proteolysis of purified factor VIII procoagulant protein: Correlation of activation with generation of a specific polypeptide, (1983) *Blood* 61:807–811.

Hybritech Data Sheet (Catalog #0432) (now Boehringer Mannheim Data Sheet, Catalog No. 1199 226 and 1199 234), Anti–factor VIII:C, human: Monoclonal antibody to human factor VIII:C blood clotting factor from mouse-–mouse hybrid cells,.

Rotblat et al., Purification of human factor VIII:C and its characterization by western blotting using monoclonal antibodies, (1985) *Biochemistry* 24:4294–4300.

Tuddenham et al., The properties of factor VIII coagulant activity prepared by immunoadsorbent chromatography, (1979) *J. Lab. Clin. Med.* 93:40–53.

Weinstein et al., Analysis of factor VIII coagulant antigen in normal, thrombin–treated, and hemophilic plasma, (1981) *Proc. Natl. Acad. Sci. USA* 78:5137–5141.

METHOD AND COMPOSITION FOR PREPARATION OF FACTOR VIIIC

This application is a continuation of application Ser. No. 07/669,680 filed on Mar. 14, 1991, now abandoned, which was a continuation of application Ser. No. 06/570,062, filed Jan. 12, 1984, now issued U.S. Pat. No. 5,004,804, issued Apr. 2, 1991.

BACKGROUND OF THE INVENTION

1. Field of the Invention

Factor VIIIC is a plasma protein that participates in the intrinsic pathway of blood coagulation. It is absent or defective in individuals with the hereditary X chromosome-linked recessive bleeding disorder hemophilia A. Great difficulty has been encountered in isolating Factor VIIIC due to its extremely low concentration in plasma and the fact that it appears to be an intermediate or final degradation product of a larger protein precursor. Therefore, efforts to isolate Factor VIIIC have led to complex mixtures of significant heterogeneity and varying molecular weights.

One of the approaches which has found broad application to the production of physiologically active proteins involves the isolation of the protein of interest in purified form. The protein of interest provides invaluable aids in the development of a recombinant DNA capability for the production of the protein. By having the protein of interest, one may prepare monoclonal antibodies which are specific for the protein and can be used to establish the production of the protein in lysates, expression from messenger RNA in oocytes, or from a cDNA gene in unicellular microorganisms. In addition, by amino acid sequencing, one can develop probes, employing codons coding for the particular amino acid sequence, for hybridization to messenger RNA, chromosomal DNA or cDNA and, therefore, provide for the detection, isolation and expression of the relevant gene or message and the production of the desired product in high yield in one or more hosts.

2. Description of the Prior Art

U.S. Pat. No. 4,361,509 and references cited therein describe purification of Factor VIIIC. See also Fulcher and Zimmerman, *Proc. Natl. Acad. Sci. USA* (1982) 79:1648–1652. Tuddenham et al., *J. of Lab. Clinical Medicine* (1979) 93:40–53 describes purification of Factor VIIIC using polyclonal antibodies. Austen, *British J. Hematology* (1979) 43:669–674 describes the use of aminohexyl-Sepharose for Factor VIIIC purification. Weinstein et al., *Proc. Natl. Acad. Sci. USA* (1981) 78:5137–5141 describes a study of the effect of thrombin on Factor VIIIC. See also Kuo et al., Abstracts for IX International Congress of Thrombosis and Hemostasis, (Copenhagen; July, 1983).

SUMMARY OF THE INVENTION

Methods and compositions are provided for production of human Factor VIIIC, precursors and subunits thereof, by expression in a microorganism or mammalian tissue culture cells. The method involves isolating pure Factor VIIIC, subunits and fragments thereof and determining their physiological relationship, particularly employing thrombin digestion. At least a portion of each of the related series of polypeptides is sequenced and the sequences employed for developing complex probes. Genomic DNA fragments are probed for homologous sequences and hybridizing fragments isolated and further manipulated to provide a DNA fragment encoding a complete subunit or fragment and/or used for isolating mature mRNA, from which ds cDNA may be obtained. The DNA sequence may then be further manipulated for insertion into an expression vector and the expression vector employed for introduction into a compatible host for expression of the polypeptide.

DESCRIPTION OF THE SPECIFIC EMBODIMENTS

Human Factor VIIIC fragments and subunits are provided in substantially pure form. In addition, methods and compositions are provided for the expression of Factor VIIIC subunits and fragments for producing Factor VIIIC as a precursor or in its active form or providing individual subunits for use in combination with naturally available subunits. The subunits and fragments have one or more biological properties associated with Factor VIIIC, such as epitopic sites, coagulation activity, and immunogenicity, so as to be used for producing antibodies which find use as reagents, particularly labeled reagents in immunoassays.

Human Factor VIIIC is a complex protein which can be isolated in substantially pure form exhibiting an apparent molecular weight of about 460 kd. Upon electrophoresis under denaturing conditions, a large number of fragments result of varying molecular weights: 240, 160, 140, 115, 92.5, 80 and 77 kd, the latter two being found to migrate as a doublet. Analysis of the fragments by chemical and protease cleavage including thrombin, employing antibodies to follow immunogenic relationships and cleavage patterns to follow structural relationships, demonstrates that the 92.5 kd polypeptide is related to the 240, 160, 140 and 115 polypeptides while the 77/80 doublet may not have common identifiable characteristics with the other peptides, except for the 240 kd polypeptide. It is further found that the 77/80 kd doublet is converted by thrombin to a 67/70 kd doublet, while the 92.5 kd polypeptide present in purified Factor VIIIC material treated with thrombin is cleaved by thrombin, directly or indirectly, into two polypeptides of about 40 and 52.5 kd. It is found that the electrophoretically isolated 77/80 kd doublet polypeptides have their N-termini blocked, while the 67/70 kd doublet polypeptides do not have their N-termini blocked.

It is further found that the locus for Factor VIIIC involves exons with large introns, where exons involve various domains associated with Factor VIIIC. Thus, individual exons can be isolated which involve specific polypeptides or fragments thereof involved with the Factor VIIIC complex. By identifying specific amino acid sequences involved with Factor VIIIC subunits and fragments thereof, one can selectively isolate the exons from genomic DNA and use the exons by themselves, in combination, or joined by synthetic DNA to provide for sequences encoding for and production of polypeptide subunits of Factor VIIIC or fragments thereof.

Conveniently, the Factor VIIIC genomic DNA sequences containing both exons and introns may be inserted into an expression vector appropriate for transcription and translation in mammalian cells to provide for both substantial quantities of properly spliced messenger RNA suitable for cDNA cloning and production of Factor VIIIC, subunits or fragments. In addition, the DNA sequences isolated from the genome can be used for hybridizing to natural messenger RNA encoding for Factor VIIIC. The messenger RNA may then be used to prepare ds cDNA for encoding the subunits of Factor VIIIC. The DNA sequences may be employed for expression by insertion into an appropriate expression vector having the necessary regulatory signals for transcription and translation. The Factor VIIIC gene expression vector (an expression vector carrying one or more genes encoding for all or a portion of Factor VIIIC, precursor, subunits or fragments thereof) may be introduced into a compatible host and the host grown for expression of Factor VIIIC. By appropriate choice of hosts, the Factor VIIIC DNA may be inserted downstream from a secretory leader and processing signals, so that the product will be secreted from the host and processed to provide for the complete polypeptide. As appropriate, the polypeptide may be further processed to introduce functionalities or substituents present on the naturally occurring polypeptide.

In the first stage of the subject invention, highly purified Factor VIIIC is obtained and characterized. Purified Factor VIIIC can be obtained from commercially available human anti-hemophilic factor (AHF), which is prepared from fresh, normal human plasma as a cryoprecipitate and represents about a 40-fold enrichment. The Factor VIIIC is further concentrated and purified by dissolving the anti-hemophilic factor into an appropriate buffer, e.g., saline imidazole-lysine-HCl, pH 7.4, followed by chromatography on an affinity column having either polyclonal or monoclonal antibodies to Factor VIII:R. Conveniently, the antibodies are covalently bonded to a Sepharose support. Factor VIIIC may be eluted from the column employing a combination of a relatively high concentration of calcium ion in combination with glycerol. The fractions obtained from the column may then be dialysed with an appropriate buffer, as described above, containing a low concentration of calcium ion and may then be further purified employing an aminohexyl-Sepharose column eluted with a high calcium or sodium chloride concentration buffer. Additional chromatographic steps, e.g., gelatin Sepharose, HPLC, ion exchange on dextran sulfate or Mono Q, affinity columns using lectins or antibodies to Factor VIIIC, provide additional purification. Particularly, the use of dextran sulfate removes trace contamination, e.g., fibrinogen, fibronectin, IgG, from the preparation, so as to leave a product substantially free of foreign proteins. Activity of the fractions from the columns may be monitored for either or both biological and antigenic activity using coagulation assay (commercially available kits) and antibodies specific for Factor VIIIC. Based on the concentration of Factor VIII in plasma, purifications of about 200,000-fold may be achieved by the above-described method.

Characterization of Factor VIIIC

Gel filtration indicates that Factor VIIIC behaves as a complex with an apparent molecular weight of about 460 kd. Using SDS-gel electrophoresis (denaturing conditions) seven individual polypeptides can be isolated of differing molecular weight. The fragments as defined by their molecular weight are 240, 160, 140, 115, 92.5, 80 and 77 kd. These fragments were characterized in the following ways.

The first study involved employing inhibitor antibodies isolated from hemophilic patients, the antibodies being designated as Z and E. Both antibodies reacted with the 77/80 kd doublet. The E antibody reacted strongly with the 240 kd polypeptide and weakly with several bands between the doublet and the 240 kd polypeptide. The Z antibody also reacted weakly with the 240 kd polypeptide.

In immunoprecipitation experiments, the E antibody precipitates the 77/80 kd doublet as well as the high molecular weight species of 160, 140, 115 and 92.5 kd, with the doublet among the stronger bands. Inclusion of EGTA results in the loss of the bands other than the doublet indicating that the 92.5 kd species is associated with the 77 kd and/or 80 kd species in a complex mediated by a $Ca^{++}$ bridge.

In the next study, monoclonal antibodies were prepared, which both inhibit Factor VIIIC mediated coagulation activity and react with components of the complex: Class I reacting with the 77/80 kd doublet and 240 kd polypeptides; Class II reacting with the 160, 140, 115 and 92.5 kd polypeptides. Immunoprecipitation of thrombin-digested Factor VIIIC with Class I antibodies indicates that the 70/67 kd doublet which results is derived from the 77/80 kd doublet present in Factor VIIIC. The Class II monoclonals indicated that the 160, 140 and 115 kd peptides are precursors of the 92.5 kd peptide. A 40 kd peptide cleavage product of 92.5 kd peptide was also bound by the Class II antibodies. An ELISA assay using monoclonal antibodies in the presence and absence of EGTA confirms the $Ca^{++}$ bridge association between the 92.5 kd and 77 kd and/or 80 kd components of the Factor VIIIC complex.

Both the human inhibitor and monclonal antibodies may be used in immunosorbent column procedures to obtain Factor VIIIC or using EGTA, to resolve its constituent components, the 92.5 kd and 77/80 kd species.

The next study involved thrombin degradation of purified Factor VIIIC material at pH 6.8 or 7.4. Aliquots were assayed for coagulation activity and TCA precipitated for gel analysis. Coagulation activity was shown to increase with time and then decrease coincidently with an increase and decrease in the amount of the 92.5 kd species. Thrombin treatment of the purified Factor VIIIC material for short periods of time (5–15 min) enhances the amount of 92.5 kd species, while the 77/80 kd doublet is partially converted to a 67/70 kd doublet. When long thrombin digestion times are employed, e.g., one hour, the 92.5 kd protein is degraded and two new peptides of 40 and 52 kd appear, with the 40 kd peptide retaining immunogenic characteristics of the 92.5 kd species. The 52 kd peptide is shown to be a cleavage product by chemical and enzymatic degradation patterns and products analogous to the 92.5 kd species.

In the next study individual Factor VIIIC subunits and precursors (e.g., 240, 77/80, 92.5 kd species) were isolated by preparative SDS gel electrophoresis and a time course thrombin digestion of the isolated polypeptides was then performed. The 240 kd fragment isolated from a preparative gel produced 160, 140, 115, and 92.5 kd bands. The 80 kd and 77 kd fragments produced a 70 kd and 67 kd fragment, respectively.

A Factor VIIIC complex is derived containing the 77 kd and/or 80 kd species and 92.5 kd polypeptide as a calcium-bridged complex in highly purified form. The purity of Factor VIIIC material (the complex and precursor species) is usually greater than 80%, often greater than 90%, and may be 98% or higher based on total protein, and that of the complex at least 20%, more usually 30% based on total protein, following the anti-Factor VIIIR immunosorbent and aminohexyl Sepharose columns. The use of additional chromatographic steps, e.g., dextran sulfate, increases the level of purity to at least 90% and usually greater for the Factor VIIIC material (complex plus precursor).

The purity of Factor VIIIC components, 92.5 kd species and the 77/80 kd doublet, isolated by preparative SDS gel electrophoresis is usually at least 98%. As indicated above, the complex can be obtained using monoclonal antibodies specific for a member of the doublet, or for the 92.5 kd polypeptide. The complex may then be separated from the antibody using a denaturing or chaiotropic solvent, e.g., aqueous urea or thiocyanate, respectively.

Preparation of Probes

A partial amino acid sequence of the N-terminus of the 67 and 70 kd polypeptides is as follows:

| 1 | 2   | 3   | 4   | 5   | 6   | 7   | 8   | 9   | 10  | 11  |
|---|-----|-----|-----|-----|-----|-----|-----|-----|-----|-----|
| ? | Phe | Gln | Lys | Lys | Thr | Arg | His | Tyr | Phe | Ile |
| 12 | 13 | 14 | 15 | 16 | 17 | 18 | 19 | 20 | 21 | 22 |
| Ala | Ala | Val | Glu | Arg | Leu | Trp | Asp | Tyr | Gly | Met |

The N-terminus amino acid sequence of the 52 kd protein is substantially as follows, particularly amino acids 1–11, where amino acids 12–18 may differ by from 1 to 3 amino acids:

| 1 | 2 | 3 | 4 | 5 | 6 | 7 | 8 | 9 | 10 |
|---|---|---|---|---|---|---|---|---|----|
| Ala | Val | Ala | Leu | Tyr | Tyr | Leu | Gly | Ala | Val |
| 11 | 12 | 13 | 14 | 15 | 16 | 17 | 18 | | |
| Glu | Asp | Cys | Trp | Asp | Gly | Ser | Arg | | |

Based on these sequences, probes for the 67/70 kd doublet (and thus the 77/80 kd doublet from which it is derived) were prepared having the following sequences:

```
Probe 1:  3'      GTA ATA AAA TAA CGX CGX CA   5'      (X = G,C,A,T)
                       G   G   G   G
                                   T
Probe 2:  3'      AAA GTT TTC TTC TGX TCT GT   5'
                       G   C   T   T       C
                                      GCX
Probe 3:  5'      GAA CGX TTA TGG GAT TAT GGX ATG   3'
                       G AGA   G           C   C
                         G CTX
Probe 4:
3'    TCT GTA ATG AAA TAG CGA CGA CAC CTT TCT GAC ACC CTA ATG CCG TAC   5'
          C   G       G       G   G       C   C               G
```

Isolation of DNA

The above probes can be used for the detection and isolation of either genomic DNA or messenger RNA. Cloning genomic DNA involves cleavage of the genomic DNA with one or more restriction enzymes to obtain a partial digest having primarily fragments of about 10–25 kb. The restriction digests should be incomplete so that there will be overlapping fragments cloned. These fragments may be cloned in the appropriate vector to produce a "library" of clones in microorganisms, e.g., bacteria, such as *E. coli*. Various vectors may be employed, including plasmids or viruses, such as pBR322, lambda, charon 4A, EMBL-4, or the like.

The DNA is screened with the enzymatically radiolabeled probes described above and homologous sequences detected. Those sequences which hybridize with one or more of the probes may be recloned and again rehybridized one or more times.

One or more restriction enzymes different from the original restriction enzyme(s) employed may then be used to provide for smaller fragments, generally ranging from about 1–10 kb, more usually from about 1–6 kb. These fragments may then be subcloned and screened to identify positive fragments. The synthetic probes can then be used as primers for sequencing of the DNA fragments. Fragments of particular interest include a sequence complementary to one or more of the above-identified probes, where the homologous sequence is from about 5 bases and up to not more than about 500 bases from the 5'-terminus. Other fragments of interest include those at the termini of the original cloned fragment since these will be represented in other clones in the library and thus used to "walk" along the chromosome until the entire desired gene is recovered.

After sequencing the DNA fragment, based on the determined sequence, the fragment will be further manipulated. Based on the sequence, one can identify an open reading frame including the determined amino acid sequence. By determining restriction sites, one can further reduce the size of the fragment, without loss of coding sequences, although removal of a short sequence at the N-terminus is permissible, since this can be replaced by using appropriate adapters. Where restriction sites are not readily available at appropriate positions, the DNA fragment may be modified by Bal31 resection for varying times, the resulting fragments cloned, and the 5'-termini determined by various techniques. Conveniently, one can provide for a recognition site of a particular restriction enzyme by appropriate selection of the 3'-bases to which the resected fragment is joined. In this way, one can screen the resulting clones for the predetermined restriction site, which will indicate the presence of a fragment resected to the desired site.

Desirably exons or fragments thereof, usually of at least 50 bp, more usually of at least about 100 bp, even about 250 bp or more, may be denatured and used as probes for mRNA from human cells, particularly cells producing mRNA for Factor VIIIC. By isolating hybridizing mRNA, the mRNA may be screened by translation in oocytes or a reticulocyte lysate and production of Factor VIIIC detected by antibodies to Factor VIIIC or coagulation activity based on binding to Factor VIIIC subunits. The mRNA may then be reverse transcribed, using, for example, AMV reverse transcriptase. Various methods can be used for converting ss cDNA to ds cDNA, using the reverse transcriptase or DNA polymerase I (Klenow fragment) to produce the second strand, followed by removal of the terminal loop, as appropriate, with a nuclease, e.g., $S_1$ nuclease. Where an incomplete copy is obtained, the messenger may be "walked" or primed cDNA synthesis may be used until the 5'-coding sequence of the mRNA has been copied and a DNA sequence encoding for the entire coding region of the mRNA is obtained.

Based on the above procedures, DNA sequences coding for the polypeptide precursor(s) to Factor VIIIC or major fragments thereof may be used for expression, or smaller fragments coding for specific subunits of Factor VIIIC, e.g., 92.5 kd, 80 kd or 77 kd, may be employed.

For the precursor polypeptide, (proFactor VIIIC), the gene may be blunt-ended at one or both ends and inserted into an expression vector having complementary ends, or may be cleaved downstream from the 5'-coding terminus and joined to an adapter for appropriate insertion into the vector.

Fragments having the proper N-terminus, which may be at the coding sequence for the 70 kd or 80 kd polypeptide or may have a 5'-terminus downstream from the initial base, usually not more than about 30 bases downstream, more usually not more than about 20 bases downstream, may then be inserted into an appropriate vector using adapters, as appropriate.

Various vectors may be employed for providing extrachromosomal elements, depending upon the particular host, the manner of expression, whether constitutive or induced, the desired markers, whether secretion is desired, or the like. (By vector is intended an intact replication system.) Numerous vectors are presently available which provide for the transcriptional and translational regulatory signals recognized either by mammalian hosts, e.g., tissue culture cells or by prokaryotic and eukaryotic microorganism hosts, e.g., *E. coli, B. subtilis, B. thermophilus, S. cerevisiae*, or the like.

The vectors will have a replication system recognized by the host, although in some instances, integration of a construct having transcriptional and translational regulatory signals and the cistron of interest into the host genome may be desirable. In those situations, the construct will usually be flanked by sequences homologous to sequences in the host genome.

The expression vectors which are employed will have transcriptional and translational signals recognized by the host. The transcriptional signals will include the promoter and terminator, as well as auxiliary signals such as one or more enhancers. In addition, regulation of transcription may be provided, by including operators, activators, genes providing for repression, or the like. Other sequences involved with transcription include capping, polyadenylation, etc. For translation, depending upon the host, there may be a ribosomal binding site, an initiation codon, stop codons, or the like.

Conveniently, non-coding 5'- and 3'-flanking regions will be employed from genes native to the host, so that the signals recognized by the host will be present in appropriate relationship. These flanking regions can be joined to the gene encoding for the Factor VIIIC precursor, subunit or fragment thereof, so that the gene is in reading frame with the initiation codon and either carries its own stop codon or is inserted immediately upstream from one or more stop codons.

A vector will normally have one or more markers which provide for selection and allow for continued selective pressure during growth of the host. These markers may include prototrophy in an auxotrophic host, antibiotic resistance, toxin resistance, etc.

Where a secretory leader and processing signals are provided, it will usually be necessary to provide an adapter. By providing for an appropriate restriction site at the terminus of the DNA sequence encoding secretory leader and processing signals or upstream therefrom, one can synthesize an oligonucleotide adapter, usually of from about 10–50 bp, which can be inserted between the secretory leader and processing signals or truncated portion thereof, and the gene of interest, which has a 5'-terminus at the initial codon of the gene or downstream thereof, so that the adapter restores all of the necessary missing bases and provides for the gene being in reading frame with the initiation codon of the leader sequence.

The resulting constructs which include the desired gene may then be introduced into a host, capable of growth in culture, in accordance with conventional methods, e.g., transformation, conjugation, transfection, or the like. The host may then be grown in an appropriate nutrient medium and the product isolated in accordance with conventional ways. Where the product is retained intracellularly, the cells will be harvested and lysed; where secreted, the product will be isolated from the nutrient medium. The product may be purified by chromatography, e.g., affinity chromatography, electrophoresis, extraction, HPLC, or the like.

For expression in a mammalian cell a mammalian virus may be employed as the vector, e.g., SV-40, papilloma virus, Maloney murine sarcoma virus, adenovirus, or the like. These viruses have been modified for use as expression vectors in mammalian cell cultures. An illustrative system employs COS cells bearing an integrated SV-40 genome and producing the large T antigen required for SV-40 replication (Gluzman, *Cell* (1981) 23:175). A fragment spanning the HpaI site at 0.76 on the SV-40 map to the BamHI site at 0.14 on the SV-40 map may be used as a vector. The recombinant plasmid obtained by joining the Factor VIIIC gene or portion thereof with the SV-40 vector may be used to transfect monkey CV-1 cells.

In accordance with the subject invention, purified subunits and fragments of Factor VIIIC may be obtained and used to enhance clotting capability for individuals requiring the particular subunit. proFactor VIIIC may also be used in therapy. In addition, the polypeptides prepared according to this invention can be used for the production of monoclonal antibodies to Factor VIIIC, its subunits and fragments. Also, the subunits and fragments may be used as reagents, which may be labeled and in combination with the antibodies, employed in diagnostic assays for the presence of one or more subunits or degradation fragments thereof in physiological fluids, e.g., blood or serum.

The following examples are offered by way of illustration and not by way of limitation.

Whenever used hereinafter Ab intends antibody and Ag antigen.

EXPERIMENTAL

I. Purification of Factor VIIIC

Human Factor VIIIC was isolated from commercial cryo-precipitate preparations by a) immunosorbent chromatography using a polyclonal anti VIIIR-Sepharose column by a method first described by E.G.D. Tuddenham, N. C. Trabold, J. A. Collins, and L. W. Hoyer, *J. of Lab. Clinical Medicine* (1979) 93:40; and b) a chromatographic separation on aminohexyl-substituted agarose as was originally described by D.E.G. Austen, *British J. of Hematology* (1979) 43:669.

Details of the procedures are described below.

Goat anti-human Factor VIII Related Antigen (VIII:R) serum obtained from *Atlantic Antibody* (cat. no. 040-01), was treated with either a standard 0–50% ammonium sulfate cut followed by DEAE cellulose column chromatography, or a similar 0–33% cut without subsequent chromatography. These materials were then conjugated to CNBr-activated Sepharose CL2B or 4B, respectively, (Pharmacia, 17-0140-01 or 17-0430-01) and poured as a column (anti VIII:R-Sepharose column).

"HEMOFIL", a stable, dried preparation of antihemophilic factor (Factor VIII, AHF, AHG) in concentrated form prepared from fresh, normal human plasma, representing about a 40-fold enrichment for Factor VIIIC, was dissolved in the following buffer: 0.02M imidazole, 0.15M NaCl, 0.1M lysine-HCl, 0.02% $NaN_3$, pH 7.4.

After being dissolved, the Hemofil was applied to the above-described anti VIII:R-Sepharose column. Non-specifically bound protein was eluted with the above buffer modified to 0.5M NaCl. Next, Factor VIIIC was eluted with the above buffer containing 0.35M $CaCl_2$, with the addition of 10% glycerol which stabilizes the Factor VIIIC activity. Active fractions from the immunosorbent column were pooled and dialyzed against buffer (0.02M imidazole, 0.15M NaCl, 0.1M lysine-HCl, 0.025M $CaCl_2$, 0.02% $NaN_3$, 10% glycerol, pH 7.4). An aliquot of the dialyzed fractions, which contained 1,100 units of Factor VIIIC, was applied to an aminohexyl-Sepharose 4B column (1×6 cm) equilibrated with dialysis buffer described above. Factor VIIIC activity was eluted with the same buffer containing either 0.35M $CaCl_2$ or 2M NaCl. The activity was found to be in a volume of 2 ml with 500 units of Factor VIIIC per ml. Subsequent experiments carried out in the same manner provided a recovery of 25% off the anti VIII:R column and a recovery of approximately 90% off the aminohexyl column. Alternatively, pooled, dialysed material eluted from the immunosorbent column is first applied to a dextran sulfate (Pharmacia) column (1.5×6 cm) equilibrated with the dialysis buffer above and eluted with the same buffer. Several minor contaminants, e.g., fibrinogen, fibronectin, IgG, are retained on the column while Factor VIIIC emerges in the flow-through which is collected and loaded on the aminohexyl-Sepharose column as before.

Both biological, i.e., clotting, and antigenic (cAg) activity were shown to be present in the purified Factor VIIIC, as demonstrated by the subsequent assays indicating a 5,000-fold purification over the 40-fold concentration in Hemofil. Using a standard commercially available three component kit from General Diagnostics, (APTT, Factor VIII deficient plasma, Verify Normal Citrate) a coagulation assay was carried out and indicated high levels of Factor VIIIC biological activity.

Antibodies employed were derived from inhibitor patients, one with a low titer (LZ) as coating ab and one with a high titer (HZ) as the labeled ab. The antibodies were used in two different types of assays. In an RIA assay, the HZ ab is labeled with $I^{125}$, while in an ELISA assay the HZ ab is coupled to horseradish peroxidase. Labeling with $^{125}I$ of antibody HZ for the RIA was performed in accordance with Hunter, W. M., In Radioimmunoassay, Weir, D. M., ed., Handbook of Experimental Immunology, 3rd ed., vol. 1, Blackwell Scientific Publications, Oxford, 1978. HRP-HZ conjugation was in accordance with Wilson and Nakane, In Immunofluorescence and Related Staining Techniques, Knapp et al., eds., Elsevier, North-Holland Biomedical Press, Amsterdam, 1978, pp. 215–224. LZ had an activity of 700 Bethesda Units/ml while HZ had an activity of 1,500 Bethesda Units/ml. Coating antibody (LZ) was diluted to 3.5 µg/ml in 0.1M $NaHCO_3$, pH 9.8 (RIA) or 0.05M imidazole, 0.1M NaCl, 0.01% Thimerosal, 0.05% Tween 20, 5% BSA (ELISA) or for either method PBS-CMF (for 1 liter: 200 mg KCl, 200 mg $KH_2PO_4$, 8.0 g NaCl, 1.15 g anhydrous $Na_2HPO_4$, pH 7.4) and 1 ml added to each tube (polystyrene) and incubated overnight at room temperature. This solution is removed by suction and the tubes washed 3× with 3–3.5 ml 0.15M NaCl or PBS-CMF containing 0.05% Tween 20. Samples or standards (General Diagnostics, Verifiy Normal Citrate, catalog #34112) are diluted and added to the tubes to a total volume of 0.9 ml per tube and incubated overnight at room temperature (dilutions were made in 0.02M Tris, 0.15M NaCl, 5% BSA, 0.05% Tween 20, 0.01% Thimerosal, pH 6.5 for RIA or 0.05M imidazole, 0.1M NaCl, 0.01% Thimerosal, 0.05% Tween 20, 5% BSA for ELISA or PBS-CMF for either method). Solutions were removed by suction and tubes washed as before. For RIA, $5 \times 10^5$ cpm of $^{125}I$-labeled antibody to Factor VIIIC (HZ) in 600 µl of RIA dilution buffer was added to each tube which was then incubated at 37° C. for 16–18 h; solutions were removed, the tubes washed as before and counted in a gamma counter. For ELISA, 0.9 ml peroxidase conjugated anti-Factor VIIIC (HZ) was added to each tube which was then incubated overnight at room temperature; solutions were removed and the tubes washed as before, then 0.9 ml OPD solution (for 100 ml: 0.73 g citric acid, 1.19 g disodium acid phosphate, 0.15 g o-phenylenediamine, pH 5.0 with 250 µl 10% $H_2O_2$ added immediately before use) added and incubated at room temperature for 30 min in the dark. To stop this reaction, 0.5 ml of 6N HCl (or 0.9 ml 1M $H_2SO_4$) was added to each tube and the $OD_{492}$ read.

II. Structure of the Factor VIIIC Complex

A. Immunoprecipitation Experiments

Gel filtration experiments were carried out with an AcA 44 column on the Factor VIIIC purified material under the following conditions: 0.1% insulin (as carrier protein for stabilization), 0.25M $CaCl_2$, 0.01% Thiomerosal, 0.05M imidazole, pH 7.2. The Factor VIIIC coagulation and antigenic activities of the eluate were monitored. Two antigenic peaks were observed. One with Factor VIIIC coagulation activity behaved as a complex with an apparent molecular weight of about 460,000 under these conditions (native). The other peak (devoid of coagulation activity) eluted at an observed molecular weight slightly below 67,000.

When analyzed by standard analytical Laemmli SDS-gel electrophoresis (Laemmli, Nature (1970) 227:680–685), various protein species of 240, 160, 115, 92.5, 80 and 77 kd were obtained. The relationship of these proteins to Factor VIIIC was determined by standard immunoprecipitation procedures. In the immunoprecipitation procedure, S. aureus protein A-Sepharose CL4B or polystyrene beads (⅛ in, Precision Plastic Ball Co.) coated with affinity purified second antibody (goat anti-mouse IgG or anti-human IgG) were employed to separate antigen-Ab complexes from free $^{125}I$-labeled Factor VIIIC.

The proteins eluted from the affinity column were iodinated and then reacted with antibodies specific for Factor VIIIC. The antibodies were human inhibitor antibodies isolated from hemophiliac patients and referred to as anti-Factor VIIIC (Z) and (E) or inhibitor antibody (Z) and (E).

The results indicated that both antibodies reacted with the 77/80 kd doublet. The "E" antibody also reacted strongly with the 240 kd band and gave weak precipitation of several bands (160, 140, 115, 92.5 kd) between the doublet and 240 kd species. The "Z" antibody also precipitated the 92.5 kd and 240 kd proteins. The strong reaction of the "E" antibody with the 240 kd species suggests that this species is a precursor of Factor VIIIC.

The antibody-column purified Factor VIIIC fraction was iodinated and reacted with the human inhibitor antibody in the presence and absence of EGTA (ethylene glycol bis(β-aminoethyl ether) N,N,N',N'-tetracetic acid). This allows for an investigation of the role of divalent cations, particularly $Ca^{++}$, in the association of the Factor VIIIC polypeptides. It was observed that the inhibitor antibody (E) precipitates the 77/80 kd doublet, as well as higher molecular weight species of 160, 140, 115 and 92.5 kd. The doublet is always among the stronger bands. (This immunoprecipitation experiment was done with the polystyrene beads. This procedure results in lower backgrounds and the labeled IgG in the Factor VIIIC preparation is not precipitated). Inclusion of EGTA results in the loss of the higher molecular weight bands (92.5–160 kd) but has no effect on the amount of doublet precipitated. A similar experiment utilized Z antibody coupled to Sepharose as an immunosorbent: purified Factor VIIIC is applied to the column and after binding via 77/80 kd, the 92.5 kd polypeptide is selectively eluted with EDTA (ethylene diamine tetraacetic acid). The method is used preparatively to fractionate the 92.5 kd species. This immunosorbent column or a similar one are prepared with monoclonal antibodies to Factor VIIIC. When eluted with chaotropic or denaturing solvents, e.g., thiocyanate solutions or aqueous urea, respectively, rather than EGTA, Factor VIIIC is further purified. These results suggest that the 92.5 kd peptide may be associated noncovalently to the 77/80 kd doublet via a $Ca^{++}$ bridge. Inhibitor antibody appears to interact directly only with the doublet. The higher molecular weight bands (the 115 kd, 140 kd, 160 kd) are probably precursors of 92.5 kd, as indicated by the ability of the monoclonal antibody directed against the 92.5 kd polypeptide to cross-react with the 115 kd, 140 kd and 160 kd polypeptides.

The relationship of various protein species from the affinity column was demonstrated by immunoprecipitation of iodinated, purified Factor VIIIC with monoclonal antibodies prepared according to the method of G. Kohler and C. Milstein (*Eur. J. of Immunol.* (1975) 6:511). Balb/c mice were immunized with liquid phase immunoadsorbed Factor VIIIC. Spleen cells ($10^8$) were fused with $10^7$ NSO or NSI mouse myeloma cells. The fusion products were plated into two 96-well microtiter trays. A spleen cell feeder layer was used at $10^4$ cells/well. Colonies were microscopically visible from the fifth day and the supernatants assayed every few days using an ELISA assay. The following layers were employed: 1st, monospecific anti(mouse IgG); 2nd, hybridoma cell supernatant; 3rd, cryo-precipitate containing human Factor VIIIC; 4th, HRP-IgG(LZ).

Several classes of monoclonal antibodies were identified, two of which inhibited Factor VIIIC coagulation activity: Class I antibodies reacted with the 80/77 kd doublet and 240 kd polypeptides; and Class II antibodies reacted with proteins of 240, 160, 140, 115, 92.5 kd. Immunoprecipitation of thrombin-digested Factor VIII with Class I monoclonal antibodies indicates that the 70/67 kd doublet produced is derived from 77/80 kd doublet (see below). Class II monoclonal antibodies indicate that the 160, 140 and 115 kd peptides are precursors of 92.5 kd peptide. The monoclonal antibodies of Class II further reacted with a 40 kd peptide produced by thrombin digestion of the purified Factor VIIIC material.

An experiment similar to that described above, using EGTA to investigate the role of $Ca^{++}$ ion in the Factor VIIIC complex, was also performed utilizing a monoclonal antibody based ELISA assay with the following layers: 1st, monospecific anti(mouse IgG); 2nd, Class II monoclonal antibody (anti-92.5 kd); 3rd, purified Factor VIIIC material; 4th, HRP-human inhibitor antibody to 77/80 kd. Addition of EGTA removed bound HRP activity present in the control without chelator. The fact that the Class I and II monoclonal antibodies directed to the 77/80 kd doublet and 92.5 kd proteins, respectively, are each inhibitory to Factor VIIIC coagulation activity implicates both as essential components of the Factor VIIIC complex.

B. Thrombin Activation of Factor VIIIC

Aminohexyl-concentrated, affinity-purified Factor VIIIC has been activated by thrombin (Boehringer, lot #1072302) using two different sets of pH conditions (6.8 and 7.4).

Aliquots were assayed for coagulation activity and, in addition, samples (about 2.5 units each) were TCA precipitated for gel analysis. In the first experiments, the VIIIC activity was initially 46 units/ml. This was diluted to a final concentration of 11.5 units/ml in Factor VIIIC buffer (20 mM imidazole, pH 6.8, 150 mM NaCl, 100 mM lysine, 25 mM $CaCl_2$ and 10% glycerol). The final concentration of thrombin was 0.12 unit/ml (about 1 unit of thrombin per 100 coagulation units of VIIIC). The results showed that the coagulation activity increases to about 180 units/ml then decreases to about 40 units/ml (essentially the starting value) coincidentally with a similar increase and decrease in the amount of 92.5 kd species. Thus the 92.5 kd species is implicated as part of the active Factor VIIIC complex.

Additional experiments with more concentrated Factor VIIIC preparations were carried out for the purpose of using thrombin activation in a preparative manner. To generate 92.5 kd polypeptide, thrombin was added to the purified Factor VIIIC material (pH 7.4) at a ratio of about 1000–2000 coagulation units of Factor VIIIC to 1 unit of thrombin activity and allowed to react for only a short period of time (5–15 min, depending on the Hemofil sample). The resulting product was then applied to a 7.5% preparative gel and peptides separated by electrophoresis, the gel bands cut out and electroeluted.

When thrombin digestion is carried out for a short time, the amount of 92.5 kd species can be doubled or tripled; at the same time, the 77/80 kd doublet is only partially converted to 67/70 kd species. To optimize conditions for isolation of the 67/70 kd doublet, a longer time course (greater than 1 h) thrombin digestion is carried out. In this case, the 92.5 kd species is further cleaved to produce smaller fragments. Two new peptides, 52 kd and 40 kd appear after thrombin treatment. The 40 kd peptide reacts with the monoclonal antibody directed against the 92.5 kd species and must therefore be a cleavage product. The 52 kd peptide is also derived from the 92.5 kd protein as demonstrated by a comparison of chemical and enzymatic cleavage patterns, i.e., both the 92.5 kd and 52 kd species when subjected to CNBr or endoproteinase lys C cleavage show a number of common fragments (by SDS-PAGE).

For endoproteinase lys C digestion, a weight ratio of lys C to protein of from about 1:1–100, usually 1:10, is used. In the subject digestion, 20 pmoles (4.8 μg) lys C was combined with 200 pmoles (14 pg) 70 kd polypeptide in about 100 μl 0.025M Tris-HCl, pH 7.7, 0.001M EDTA, 0.08% SDS and the mixture incubated at 37° C. for 6 h to overnight for complete digestion. Native polyacrylamide gels according to Orstein, *Ann. N.Y. Acad. Sci.* (1964) 121:321–349 were used for isolation of lys C digestion products.

C. Thrombin Digestion of Gel Isolated VIIIC-related Proteins

In order to confirm the precursor-product relationship of these peptides, a number of the bands were isolated by preparative SDS gel electrophoresis, electroeluted and subjected to thrombin digestion. The results were as follows:

1. The 240 kd protein produced multiple bands including 160, 140, 115, 92.5 kd but nothing smaller than 92.5 kd, i.e., no 77/80 kd or 67/70 kd doublet. In addition, a time course for digestion was carried out with the 240 kd fragment and analyzed for gel electrophoresis pattern, coagulation activity, and Factor VIIIC antigenic (Cag) activity. Gel results were the same as above and essentially no Cag or coagulation activity was recovered.

2. The 160 kd and 92.5 kd gel-isolated polypeptides do not appear to be substrates for thrombin after isolation from the gel.

3. Thrombin specifically cleaves gel isolated 77 kd and 80 kd species to produce new polypeptides of 67 kd and 70 kd, respectively. After thrombin treatment, monoclonal antibodies of Class I precipitate not only the 77/80 kd doublet, but also the new 67 and 70 kd species. When the gel-isolated 80 and 77 kd species are subjected to sequence analysis, it is found that their amino termini are blocked. When the 70 and 67 kd species are sequenced, their amino termini are not blocked. Subsequent electrophoretic analysis, together with the amino acid sequence results, indicate that the gel-isolated 77/80 kd, 67/70 kd, 92.5 kd and 52 kd polypeptides are obtained at >95%, usually 98%, purity.

D. Amino Acid Sequence Analysis

Partial amino acid sequence information was obtained by a standard procedure for the 67/70 kd peptides and the 52 kd peptide. The peptides were applied to a gas phase protein sequencer (Applied Biosystems). The PTH-amino acids were applied to an HPLC column (IBM cyano, 25 cm) and the amino sequence determined from the resulting chromatograms.

For the 67/70 kd doublet, is found the following sequence at its amino terminus:

| 1 | 2   | 3   | 4   | 5   | 6   | 7   | 8   | 9   | 10  | 11  |
|---|-----|-----|-----|-----|-----|-----|-----|-----|-----|-----|
| ? | Phe | Gln | Lys | Lys | Thr | Arg | His | Tyr | Phe | Ile |
| 12  | 13  | 14  | 15  | 16  | 17  | 18  | 19  | 20  | 21  | 22  |
| Ala | Ala | Val | Glu | Arg | Leu | Trp | Asp | Tyr | Gly | Met |

For the 52 kd protein, which as shown above is derived from the 92.5 kd protein, the following amino acid sequence is indicated:

| 1   | 2   | 3   | 4   | 5   | 6   | 7   | 8   | 9   | 10  |
|-----|-----|-----|-----|-----|-----|-----|-----|-----|-----|
| Ala | Val | Ala | Leu | Tyr | Tyr | Leu | Gly | Ala | Val |
| 11  | 12  | 13  | 14  | 15  | 16  | 17  | 18  |     |     |
| Glu | Asp | Cys | Trp | Asp | Gly | Ser | Arg |     |     |

Using the information provided by the amino acid sequence of the N-terminal region of the 67, 70 kd protein the following oligonucleotide probes were synthesized to be used to screen human genomic libraries. The phosphoramidite method as described by M. S. Urdea et al., *Proc. Natl. Acad. Sci. USA* (1983) 80: was used:

E. Preparation of Human 4X Genomic Library

Approximately 3 mg of DNA were prepared from cell culture lysates of GM1416 cells (human lymphoblastoid cell line containing 4 copies of the X chromosome).

This DNA was partially digested with the restriction enzyme Sau3A, and the digested DNA 400–500 µg) fractionated on 10%–40% sucrose gradients. Fractions in the size range 10–25 kilobases were pooled, dialyzed into Tris-EDTA and purified over Schliecher and Scheull Elutip-d sterile disposable columns. Aliquots of this DNA were ligated to EMBL-4 arms, obtained after digestion with BamHI and SalI and isolation on a gradient, and then packaged into bacteriophage lambda with an efficiency of $1\times10^6$ pfu/µg of insert DNA. The vector used, EMBL-4, is a modified form of bacteriophage lambda (see Karn et al., *Methods Enzymol.* (1983) 101:3–19). The total library consisted of $5\times10^6$ phage.

F. Plating and Screening of Human 4X Genomic Library

Bacteriophage were adsorbed to *E. coli* strain DP50 and 20 plates were plated at 50,000 pfu per plate, (150×15 mm size) to give $1\times10^6$ pfu total. (Details of techniques for plates, top agar, adsorption and plating are found in *Molecular Cloning, A Laboratory Manual*, by T. Maniatis, E. F. Fritsch and J. Sambrook; Cold Spring Harbor Lab, New York, 1982.)

Nitrocellulose filters were applied to the surface of each plate containing phage plagues (so that molecules of unpackaged phage DNA are transferred to the filters) in duplicate, and hybridized with $^{32}$P-labeled 256-fold degenerate 48-mer probe DNA (probe #4). (Details of the nitrocellulose transfer technique are found in Maniatis et al., supra.) Pre-hybridization and hybridization were carried out in Wallace mix which contains in one liter: 310 ml of distilled $H_2O$, 200 ml 50% dextran sulfate, 180 ml 1M Tris-HCl, pH 8.0, 225 ml 4M NaCl, 20 ml 0.25M EDTA, 50 ml 100X Denhardt's solution, 5 ml 100% NP-40 and 10 ml 10% SDS.

```
Probe 1:  3'     GTA ATA AAA TAA CGX CGX CA    5'      (X = G,C,A,T)
                          G   G   G   G
                                      T
Probe 2:  3'     AAA GTT TTC TTC TGX TCT GT    5'
                          G   C   T   T   C
                                      GCX
Probe 3:  5'     GAA CGX TTA TGG GAT TAT GGX ATG  3'
                     G AGA   G            C   C
                         G CTX
Probe 4:
   3'   TCT GTA ATG AAA TAG CGA CGA CAC CTT TCT GAC ACC CTA ATG CCG TAC   5'
            C   G       G       G   G       C   C               G
```

A scheme showing regions of amino acid sequence from which each probe is derived is shown below:

The probe was labeled by enzymatic transfer of $^{32}PO_4$ from γ-ATP$^{32}$ to the 5' phosphate end of each probe DNA

```
 1   2   3   4   5   6   7   8   9   10  11  12  13  14  15  16  17  18  19  20  21  22
 ?  Phe Gln Lys Lys Thr Arg His Tyr Phe Ile Ala Ala Val Glu Arg Leu Trp Asp Tyr Gly Met

AAA GTT TTC TTC TGX TCT GTA ATA AAA TAA CGX CGX CA    GAA CGX TTA TGG GAT TAT GGX ATG
          G   C   T   T   GCC  G   G   G   G                    G AGA   G            C   C
                          G                T                        G CTX
                          A
        PROBE 2-20mer (512)
        20-55% GC                 PROBE 1-20mer (384)        PROBE 3-24mer (1152)
        T_m = 48-62° C.           30-60% GC                  38-63% GC
                                  T_m = 52-64° C.            (T_m = 66-78° C.)
                              PROBE 4-48mer (256)
``` molecule, catalysed by T4 polynucleotide kinase. The hybridization conditions were as follows: 10 ml hybridization mix/filter×5000 cpm of labeled probe #4/degeneracy/ml. Hybridization was carried out at 37° C. overnight. Filters were washed in 6XSSC, 1 mM EDTA at 50°–55° C., air dried and used to expose X-ray film.

G. Characterization of Positive Clones

Twenty-three plaques giving positive signals for the first round of screening were replated, phage DNA transferred to nitrocellulose and hybridized with freshly labeled probe #4 (secondaries). Eleven plaques giving positive signals were replated, phage DNA transferred to nitrocellulose and hybridized with freshly labeled probe #4 (tertiaries). Eight plaques giving positive signals were isolated and DNA prepared (100 ml liquid cultures for each). The DNA corresponding to each of these 8 clones was digested with EcoRI (to release inserted human genomic DNA from the lambda vector DNA) and the resulting fragments separated by size using electrophoresis on a 0.8% agarose gel, denatured and transferred to nitrocellulose. This was done in quadruplicate and each filter hybridized with $^{32}$P-labeled probe #'s 1, 2, 3 or 4. The filters were used to expose to X-ray film and a single band of 4.3 kb in size was found to hybridize with all four probes for two clones. These two clones were identical except that one had 1.3 kb more insert DNA than the other (clone designations are 23 D for the larger insert of 14.43 kb and 11 for the smaller insert of 13.13 kb). The entire EcoRI digest of 23 D-DNA was subcloned in the vectors M13 and pUC-9 (a derivative of pBR322) and in addition, the 4.3 kb gel isolated EcoRI fragment subcloned in both vectors. DNA sequencing by the dideoxy technique on M13 DNA using the synthetic probe #3 and its reverse complement as primers was carried out.

The 4.3 kb fragment was partially sequenced and has the following sequence encompassing the probe #4 sequence, indicated in parenthesis, and the partial amino acid sequence of the 67/70 kd fragment originally determined, indicated in brackets.

| | 1 | | | | | | | | | 10 | | | | |
|---|---|---|---|---|---|---|---|---|---|---|---|---|---|---|
| | val | ser | phe | phe | arg | ala | gln | arg | glu | arg | leu | ser | gly | asn |
| GG | GTG | TCC | TTC | TTC | AGG | GCT | CAG | AGG | GAG | CGA | TTA | AGT | GGC | AAC |

| | | | | | 20 | | | | | | | | | |
|---|---|---|---|---|---|---|---|---|---|---|---|---|---|---|
| glu | ala | asn | arg | pro | gly | lys | leu | pro | phe | leu | arg | val | ala | thr |
| GAA | GCA | AAC | AGG | CCT | GGA | AAA | CTT | CCC | TTT | CTG | AGA | GTA | GCA | ACA |

| 30 | | | | | | | | | 40 | | | | | |
|---|---|---|---|---|---|---|---|---|---|---|---|---|---|---|
| glu | thr | leu | gln | arg | leu | pro | pro | ser | tyr | trp | ile | leu | leu | leu |
| GAA | ACT | CTG | CAA | AGA | CTC | CCT | CCA | AGC | TAT | TGG | ATC | CTC | TTG | CTT |

| | | | | 50 | | | | | | | | | | |
|---|---|---|---|---|---|---|---|---|---|---|---|---|---|---|
| gly | ile | pro | leu | trp | tyr | ser | glu | tyr | gln | lys | lys | ser | gly | lys |
| GGG | ATA | CCA | CTA | TGG | TAC | TCA | GAG | TAC | CAA | AAG | AAG | AGT | GGA | AAG |

| 60 | | | | | | | | | 70 | | | | | |
|---|---|---|---|---|---|---|---|---|---|---|---|---|---|---|
| ser | gln | glu | lys | ser | pro | glu | lys | thr | ala | phe | lys | lys | lys | asp |
| TCC | CAA | GAG | AAG | TCA | CCA | GAA | AAA | ACA | GCA | TTT | AAG | AAA | AAG | GAT |

| | | | | 80 | | | | | | | | | | |
|---|---|---|---|---|---|---|---|---|---|---|---|---|---|---|
| thr | ile | leu | ser | leu | asn | ala | cys | glu | ser | asn | his | ala | ile | ala |
| ACC | ATT | TTG | TCC | CTG | AAC | GCT | TGT | GAA | AGC | AAT | CAT | GCA | ATA | GCA |

| 90 | | | | | | | | | 100 | | | | | |
|---|---|---|---|---|---|---|---|---|---|---|---|---|---|---|
| ala | ile | asn | glu | gly | gln | asn | lys | pro | glu | ile | glu | val | thr | trp |
| GCA | ATA | AAT | GAG | GGA | CAA | AAT | AAG | CCC | GAA | ATA | GAA | GTC | ACC | TGG |

| | | | | 110 | | | | | | | | | | |
|---|---|---|---|---|---|---|---|---|---|---|---|---|---|---|
| ala | lys | gln | asn | arg | thr | glu | arg | leu | cys | ser | gln | asn | pro | pro |
| GCA | AAG | CAA | AAT | AGG | ACT | GAA | AGG | CTG | TGC | TCT | CAA | AAC | CCA | CCA |

| 120 | | | | | | | | | 130 | | | | | |
|---|---|---|---|---|---|---|---|---|---|---|---|---|---|---|
| val | leu | lys | arg | his | gln | arg | glu | ile | thr | arg | thr | thr | leu | gln |
| GTC | TTG | AAA | CGC | CAT | CAA | CGG | GAA | ATA | ACT | CGT | ACT | ACT | CTT | CAG |

| | | | | 140 | | | | | | | | | | |
|---|---|---|---|---|---|---|---|---|---|---|---|---|---|---|
| ser | asp | gln | glu | glu | ile | asp | tyr | asp | asp | thr | ile | ser | val | glu |
| TCA | GAT | CAA | GAG | GAA | ATT | GAC | TAT | GAT | GAT | ACC | ATA | TCA | GTT | GAA |

| 150 | | | | | | | | | 160 | | | | | |
|---|---|---|---|---|---|---|---|---|---|---|---|---|---|---|
| met | lys | lys | glu | asp | phe | asp | ile | tyr | asp | glu | asp | glu | asn | gln |
| ATG | AAG | AAG | GAA | GAT | TTT | GAC | ATT | TAT | GAT | GAG | GAT | GAA | AAT | CAG |

| | | | | 170 | | | | | | | | | | |
|---|---|---|---|---|---|---|---|---|---|---|---|---|---|---|
| ser | pro | arg | ser | [ phe | gln | lys | lys | thr | ( arg | his | tyr | phe | ile | ala |
| ARG | CCC | CGC | AGC | [ TTT | CAA | AAG | AAA | ACA | ( CGA | CAC | TAT | TTT | ATT | GCT |

```
180                                                          190
ala  val  glu  arg  leu  trp  asp  tyr  gly  met  ) ] ser  ser  ser  pro  his
GCA  GTG  GAG  AGG  CTC  TGG  GAT  TAT  GGG  ATG       AGT  AGC  TCC  CCA  CAT 200
val  leu  arg  asn  arg  tyr  glu  cys  ile  gly  tyr  ser  phe  ala  leu
GTT  CTA  AGA  AAC  AGG  TAT  GAA  TGC  ATT  GGT  TAT  TCC  TTT  GCT  CTG 210  211
leu  leu  OP
CTC  TTG  TGA  CATTTGACTTTACCAGATGATGACACCAACC
```

This clone thus corresponds to the gene for the 77/80 kd doublet protein, which, as it has been shown above, corresponds in part to the human Factor VIIIC complex.

To prepare Factor VIIIC, the DNA sequences from Clone 23 or Clone 11 are inserted into an SV-40 promoter as described by Laub et al., *J. Virology* (1983) 48:271, so as to be under the control of the SV-40 early promoter. The resulting recombinant plasmid may be transfected into COS cells (Guzman, supra.). Alternatively, the coding sequence can be inserted into a plasmid, e.g., pBR322, into which has been inserted the long terminal repeats of Maloney murine sarcoma virus, so that the Clone 23 or 11 sequences are under the transcriptional control of the viral regulatory system. The constructs may then be introduced into 3T3 mouse fibroblasts for efficient expression (see Perkins et al., *Molecular and Cellular Biology*, June 1983, Vol. 3, No. 6, p. 1123).

The above results demonstrate that genomic DNA has been isolated which codes for subunits of the Factor VIIIC complex. By use of this genomic DNA, the DNA may be further manipulated to provide for a sequence encoding for Factor VIIIC complex subunits. The DNA may then be used in an expression vector for production of the Factor VIIIC subunits, which may be used in a variety of ways, for example, as reagents in diagnostic assays, as therapeutic agents, for the production of monoclonal or polyclonal antibodies, which may then be used for the purification of Factor VIIIC complex or other purposes. The genomic DNA sequences may also be used for isolation of mRNA encoding proFactor VIIIC to provide for the precursor protein. This protein may then be administered for in vivo processing.

The subject techniques have provided a DNA sequence which includes the specific sequence at or adjacent to the 5'-terminus of the sequence coding for the 67/70 kd doublet, which specific sequence is also present in the 77/80 kd doublet, about 200 to 400, more exactly about 275 to 325 bases downstream from the 5'-terminus.

Although the foregoing invention has been described in some detail by way of illustration and example for purposes of clarity of understanding, it will be obvious that certain changes and modifications may be practiced within the scope of the appended claims.

What is claimed is:

1. A monoclonal antibody capable of specifically binding under binding conditions to a 77/80 kD doublet Factor VIII:C polypeptide but not to a 92.5 kD Factor VIII:C polypeptide, wherein the 77/80 kD doublet polypeptide is capable of forming a calcium-bridged complex with a 92.5 kD polypeptide, and wherein the complex exhibits a biological activity of Factor VIII:C, and the doublet polypeptide comprises an N-terminal amino acid sequence as follows:

Phe-Gln-Lys-Lys-Thr-Arg-His-Tyr-Phe-Ile-Ala-Ala-Val-Glu-Arg-Leu-Trp-Asp-Tyr-Gly-Met.

* * * * *